US008500713B2

(12) United States Patent
Ferek-Petric

(10) Patent No.: US 8,500,713 B2
(45) Date of Patent: Aug. 6, 2013

(54) IMPLANTABLE ELECTROPORATION THERAPY DEVICE AND METHOD FOR USING SAME

(75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 2335 days.

(21) Appl. No.: 10/695,848

(22) Filed: Oct. 29, 2003

(65) Prior Publication Data

US 2005/0096584 A1 May 5, 2005

(51) Int. Cl.
*A61M 31/00* (2006.01)
*A61K 9/22* (2006.01)

(52) U.S. Cl.
USPC ............... 604/500; 604/890.1; 604/891.1

(58) Field of Classification Search
USPC ........... 604/500, 502, 503, 506, 890.1, 891.1, 604/892.1
See application file for complete search history.

(56) References Cited

U.S. PATENT DOCUMENTS

| 4,556,063 | A |   | 12/1985 | Thompson et al. ...... 128/419 PT |
|---|---|---|---|---|
| 5,099,838 | A |   | 3/1992 | Bardy ........................ 128/419 D |
| 5,314,430 | A |   | 5/1994 | Bardy .............................. 607/5 |
| 5,354,319 | A |   | 10/1994 | Wyborny et al. ............... 607/32 |
| 5,386,837 | A | * | 2/1995 | Sterzer .......................... 128/898 |
| 5,389,069 | A | * | 2/1995 | Weaver ........................... 604/21 |
| 5,468,223 | A |   | 11/1995 | Mir ................................. 604/51 |
| 5,547,467 | A |   | 8/1996 | Pliquett et al. .................. 604/20 |
| 5,667,491 | A |   | 9/1997 | Pliquett et al. .................. 604/50 |
| 5,674,267 | A |   | 10/1997 | Mir et al. ......................... 607/72 |
| 5,749,847 | A |   | 5/1998 | Zewert et al. ................... 604/49 |
| 5,869,326 | A |   | 2/1999 | Hofmann .................. 435/285.2 |
| 5,888,530 | A |   | 3/1999 | Netti et al. ..................... 424/423 |
| 6,085,115 | A |   | 7/2000 | Weaver et al. ................ 600/509 |
| 6,120,493 | A | * | 9/2000 | Hofmann ....................... 604/506 |
| 6,152,882 | A | * | 11/2000 | Prutchi .......................... 600/509 |
| 6,233,482 | B1 |   | 5/2001 | Hofmann et al. ............... 604/21 |
| 6,261,280 | B1 | * | 7/2001 | Houben et al. ................. 604/500 |
| 6,592,519 | B1 | * | 7/2003 | Martinez ....................... 600/309 |
| 6,733,485 | B1 | * | 5/2004 | Whitehurst et al. .......... 604/500 |
| 2002/0077676 | A1 |   | 6/2002 | Schroeppel et al. |

FOREIGN PATENT DOCUMENTS

WO          00/74773          12/2000

OTHER PUBLICATIONS

A validated model of in vivo electric field distribution in tissues for electrochemotherapy and for DNA electrotransfer for gene therapy / Damijan Miklavcic, Dejan Semrov, Halima Mekid, and Lluis M. Mir / Biochimica et Biophysica Acts 1523 (2000) 73-83.
Electrical field and current distributions in electrochemotherapy / Kostadin Brandisky & Ivan Daskalov / Bioelectrochemistry and Bioengetics 48 (1999) 201-208Therapeutic perspectives of in vivo cell electropermeabilization / Lluis M. Mir / Bioelectrochemistry 53 (2000) 1-10.
In vivo cell electrofusion / H. Mekid and L.M. Mir / Biochimical et Biophysica Acta 1524 (2000) 118-130.

(Continued)

*Primary Examiner* — Bhisma Mehta
(74) *Attorney, Agent, or Firm* — Reed A. Duthler; Stephen W. Bauer

(57) ABSTRACT

IMDs and methods are provided for electroporation treatment of subcutaneous tumors. In some embodiments, IMDs of the present invention may store and introduce chemotherapy drugs into the body prior to electroporation therapy. High frequency stimulation of tissue in or around the tumor may also be provided to increase tissue temperature prior to electroporation therapy. Still further, delivery of the electroporation therapy may be synchronized with cardiac qRs complex to avoid impeding normal cardiac rhythm. Algorithms to suspend therapy in the event of edema may also be incorporated.

19 Claims, 11 Drawing Sheets

OTHER PUBLICATIONS

A Potential Approach for Electrochemotherapy Against Colorectal Carcinoma Using a Clinically Available Alternating Current System with Bipolar Snare in a Mouse Model / S. Kuriyama, H. Tsujinoue, Y. Toyokawa, A. Mitoro, T. Nakatani, H. Yoshiji T. Tsujimoto & H. Fukui / Scand J Gastroenterol 2001 (3).

Treatment of hepatocellular carcinoma in a rat model using electrochemotherapy / M.J. Jaroszeski, D. Coppola, & R. Heller / European Journal of Cancer 37 (2001) 422-430.

Theory and iv vivo application of Electroporative Gene Delivery / Stella Somiari, Jill Glasspool-Malone, Joseph J. Drabick, Richard A. Gilbert, Richard Heller, Mark J. Jaroszeski and Robert W. Malone / Molecular Therapy vol. 2, No. 3 Sep. 2000.

Mechanisms of electrochemotherapy / Lluis M. Mir & Stephane Orlowski / Advanced Drug Deliver), Reviews 35 (1999) 107-118.

* cited by examiner

IMPLANTABLE ELECTROPORATION THERAPY DEVICE AND METHOD FOR USING SAME

FIELD OF THE INVENTION

The present invention relates to implantable medical devices and, more particularly, to implantable electroporation therapy devices and methods and systems for using the same.

BACKGROUND OF THE INVENTION

Cell membranes provide natural resistance to entry of foreign molecules into the cell cytoplasm. As a result, the effectiveness of many cancer treatment drugs, e.g., chemotherapy agents, is somewhat limited due to the inability of the drugs to penetrate the membrane of the targeted cancer cells.

One known solution to this problem is to increase the dosage of the cancer treatment drug in an effort to provide the desired drug quantity to the targeted cells. However, such elevated dosages may often result in damage to healthy host cells proximate the targeted cells. Therefore, a system and method for introducing a cancer treatment drug into target cells while minimizing the effects on healthy host cells would be beneficial.

To address the problems associated with increased dosage, drug delivery techniques using some degree of cellular stimulation are known. For example, U.S. Pat. No. 5,888,530 to Netti et al. describes a method for enhancing drug delivery by creating a transient differential between a target tissue site and a region near the target tissue site. U.S. Pat. No. 5,386,837 to Sterzer describes a non-invasive technique for applying high frequency wave energy (e.g., RF, microwave, infrared, or ultrasonic) to create transient pores in the membranes of targeted cells through which drug molecules may enter.

Another technique known as electroporation has also been used. Electroporation is a process wherein electrical fields are applied across target cells, usually through the application of multiple electrical pulses. These pulses create transient pores through the cell membrane, yet do not result in permanent cell damage. Molecules of chemotherapeutic drugs delivered during the electroporation process may then more easily enter the cell through these temporary pores.

While promising, most clinical applications of electroporation are presently directed to cutaneous diseases such as melanoma, head and neck squamous cell carcinoma, basal cell carcinoma, and adenocarcinoma.

One cancer treatment electroporation technique is described in U.S. Pat. No. 5,468,223 to Mir. The '223 patent describes delivering a drug followed by transcutaneous electric pulses provided via external electrodes.

Another technique is disclosed in U.S. Pat. No. 5,389,069 to Weaver. The '069 patent discloses placing an electrically conductive penetrator into or proximate the target cells and an electrode on the organism surface. A voltage is then applied between the penetrator and the electrode, causing electroporation of the cells in between.

U.S. Pat. No. 5,674,267 to Mir et al. describes a needle array for introduction into the tissue to be treated. The needle array may produce an electrical pulse between each different pair of needles. U.S. Pat. No. 6,233,482 to Hofmann et al. also discloses an apparatus for in vivo electroporation using a needle array having selectable array switching patterns.

U.S. Pat. Nos. 5,547,467 and 5,667,491, both to Pliquett et al., disclose application of medication to the epidermis of an organism after which the epidermis is electroporated. U.S. Pat. No. 5,749,847 to Zewert et al. describes a similar process for delivering a nucleotide into an organism.

U.S. Pat. No. 6,085,115 to Weaver et al. also describes biopotential measurement by electroporation of a tissue surface, e.g., a skin surface.

Accordingly, electroporation devices are known. While effective for their respective intended purposes, the techniques and apparatus described herein above generally require external attachment or external introduction of the electroporation electrodes and completion of a medical procedure for each chemotherapy session.

A summary of the documents described herein above (as well as others) is provided in Table 1 below.

TABLE 1

| U.S. Pat. No. | Inventor | Issue Date |
| --- | --- | --- |
| 5,468,223 | Mir | Nov. 21, 1995 |
| 5,386,837 | Sterzer | Feb. 7, 1995 |
| 5,389,069 | Weaver | Feb. 14, 1995 |
| 5,547,467 | Pliquett et al. | Aug. 20, 1996 |
| 5,667,491 | Pliquett et al. | Sep. 16, 1997 |
| 5,674,267 | Mir et al. | Oct. 7, 1997 |
| 5,749,847 | Zewert et al. | May 12, 1998 |
| 5,869,326 | Hofmann | Feb. 9, 1999 |
| 5,888,530 | Netti et al. | Mar. 30, 1999 |
| 6,085,115 | Weaver et al. | Jul. 4, 2000 |
| 6,233,482 | Hofmann et al. | May 15, 2001 |

All documents listed in Table 1 above are hereby incorporated by reference herein in their respective entireties. As those of ordinary skill in the art will appreciate readily upon reading the Summary of the Invention, Detailed Description of the Embodiments, and claims set forth below, at least some of the devices and methods disclosed in the documents of Table 1 and others documents incorporated by reference herein may be modified advantageously by using the teachings of the present invention. However, the listing of any such document in Table I, or elsewhere herein, is by no means an indication that such documents are prior art to the present invention.

SUMMARY OF THE INVENTION

The present invention has certain objects. That is, various embodiments of the present invention provide solutions to one or more problems existing in the art with respect to intracellular substance delivery and, in particular, to intracellular cancer drug delivery. One such problem is that current treatments that take advantage of electroporation techniques are limited in their application to externally administered procedures. Thus, repeated medical procedures may be required. Moreover, current electroporation techniques do not actively monitor various physiological or biological parameters, such as temperature, edema, and drug concentration. As a result, treatment results may vary and undesirable side effects may occur.

In comparison to known electroporation techniques, various embodiments of the present invention may provide one or more of the following advantages. For instance, electroporation therapy utilizing implantable devices in accordance with embodiments of the present invention may deliver therapy at any time without medical intervention. Further, devices and methods of the present invention may attempt to optimize therapy results and minimize chemotherapy side effects by monitoring various biological parameters. For example, localized body temperature and/or drug concentration may be monitored and/or controlled by the device before actual electroporation therapy delivery. Edema detection capability may also be incorporated and may be used to suspend therapy where appropriate.

Body-implantable electroporation devices of the present invention may provide one or more of the following features, including: a housing; at least one lead extending from the housing wherein the at least one lead has a therapy electrode associated therewith, the therapy electrode operable to selectively electroporate tissue within the body; logic and control circuitry located within the housing and operable to control the therapy electrode; sensor circuitry associated with the housing, wherein the sensor circuitry may be operable to sense a biological parameter and provide a sense signal to the logic and control circuitry in response to the biological parameter, wherein the sense signal may include a feedback signal that at least partially controls the electroporation device; an energy source associated with the housing; a current converter coupled to the energy source; an electrical pulse generator associated with the housing and operable to deliver at least one electrical pulse to the body via the therapy electrode, wherein the at least one electrical pulse may produce an electric field strength of about 700 V/cm to about 1500 V/cm and have a pulse width of about 50 microseconds to about 200 microseconds; a high frequency generator associated with the housing and operable to deliver a high frequency stimulus to the body via the therapy electrode; electrocardiogram circuitry operable to measure an electrocardiogram of the body and detect a qRs complex from the electrocardiogram; impedance measuring circuitry operable to measure impedance between a portion of the at least one lead and either the housing or a second lead; telemetry circuitry coupled to the logic and control circuitry, the telemetry circuitry operable to wirelessly communicate with a programming device located outside the body, memory circuitry coupled to the logic and control circuitry operable to store information associated with the electroporation device; a drug catheter associated with the housing, the drug catheter operable to deliver a drug to the body under control of the logic and control circuitry, wherein the drug catheter is incorporated in the at least one lead; and a drug reservoir associated with the housing, wherein the drug reservoir is in fluid communication with the drug catheter.

Other embodiments of an electroporation treatment device for implantation within a body may include one or more of the following features: a housing; a first lead extending from the housing, the first lead having a first therapy electrode located proximate a distal end of the first lead; a second lead extending from the housing, the second lead having a second therapy electrode located proximate a distal end of the second lead, wherein one or both of the first therapy electrode and the second therapy electrode are operable to selectively electroporate tissue within the body; logic and control circuitry located within the housing and operable to control one or both of the first therapy electrode and the second therapy electrode; a drug concentration sensor associated with one or both of the first lead and the second lead; a temperature sensor associated with one or both of the first lead and the second lead; sensor circuitry in communication with the logic and control circuitry, the sensor circuitry operable to receive and process signals received from one or both of a drug concentration sensor and a temperature sensor; an electrical pulse generator associated with the housing, the electrical pulse generator operable to deliver one or more voltage pulses to the body via one or both of the first therapy electrode and the second therapy electrode; a high frequency generator associated with the housing, the high frequency generator operable to deliver a high frequency stimulus to the body via one or both of the first therapy electrode and the second therapy electrode; impedance measuring circuitry associated with the housing, the impedance measuring circuitry operable to measure impedance between two or more of the first therapy electrode, the second therapy electrode, and the housing; telemetry circuitry associated with the housing, the telemetry circuitry operable to permit wireless communication between the logic and control circuitry and a programming device located outside the body; memory circuitry coupled to the logic and control circuitry, the memory circuitry operable to store information associated with the electroporation treatment device; and electrocardiogram circuitry operable to measure an electrocardiogram of the body and detect a qRs complex from the electrocardiogram.

Further, some embodiments of a method for treating a cancerous tumor according to the present invention include one or more of the following features: implanting an electroporation device in a body; delivering a drug to the body and proximate the cancerous tumor; delivering, with the electroporation device, at least one electrical pulse across at least a portion of the cancerous tumor; sensing at least one biological parameter and providing a sense signal based on the biological parameter; controlling delivery of the at least one electrical pulse based on the sense signal; detecting a qRs complex from an electrocardiogram of the body and synchronizing the delivering of the at least one electrical pulse with the qRs complex; measuring impedance across a portion of the cancerous tumor and comparing the impedance to a threshold impedance value, and suspending delivery of additional electrical pulses based on a result of comparing the impedance to the threshold impedance value; increasing a temperature of the body in the vicinity of the cancerous tumor prior to delivering the at least one electrical pulse, wherein increasing the temperature of the body in the vicinity of the cancerous tumor may include delivering a high frequency stimulus with the electroporation device; and programming the electroporation device to deliver a particular therapy profile, wherein programming the electroporation device may occur after implantation.

Still further, some embodiments of a method for treating cancer according to the present invention include one or more of the following features: implanting an electroporation device in a body, the electroporation device operable to selectively-electroporate tissue within the body using at least one lead having a therapy electrode associated therewith; locating the therapy electrode in or proximate a cancerous tumor; applying a high frequency stimulus in the vicinity of the cancerous tumor with the at least one therapy electrode, thereby raising a temperature in the vicinity of the cancerous tumor; delivering a drug to the body in the vicinity of the cancerous tumor; delivering, with the electroporation device, at least one electrical pulse in the vicinity of the cancerous tumor; sensing the temperature in the body and providing a sense signal based on the temperature; detecting a qRs complex from an electrocardiogram of the body and synchronizing the delivering of the at least one electrical pulse with the qRs complex; measuring impedance across a portion of the cancerous tumor and comparing the impedance to a threshold impedance value, wherein suspending delivery of additional electrical pulses based on a result of comparing the impedance to the threshold impedance value may occur; delivering the drug through a drug catheter coupled to a housing of the electroporation device, the drug catheter in fluid communication with a drug reservoir located within the housing; delivering the drug via an external drug delivery apparatus; delivering about four to about eight electrical pulses, wherein the electrical pulses may produce an electric field strength of about 700 V/cm to about 1500 V/cm and have a pulse width of about 50 microseconds to about 200 microseconds; and programming the electroporation device to deliver a specific therapy profile, wherein programming the electroporation device may occur after implantation.

Yet still further, some embodiments of a system for treating a cancerous tumor according to the present invention may include one or more of the following features: an implantable and programmable electroporation device, having: a housing; at least one lead extending from the housing, the at least one lead having a therapy electrode associated therewith, the therapy electrode operable to selectively electroporate tissue within the body; logic and control circuitry located within the housing and operable to control the therapy electrode; and first telemetry circuitry associated with the logic and control circuitry. The system may also include the following other features: an external programming device, having: programming circuitry operable for use in programming the implantable and programmable electroporation device; and second telemetry circuitry associated with the programming circuitry, wherein the second telemetry circuitry is operable to communicate with the first telemetry circuitry to permit programming of the implantable and programmable electroporation device. The first telemetry circuitry and the second telemetry circuitry may be operable to permit bi-directional communication.

The above summary of the invention is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The present invention will be further described with reference to the drawings, wherein.

DETAILED DESCRIPTION OF THE PREFERRED EMBODIMENTS

In the following detailed description of the embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
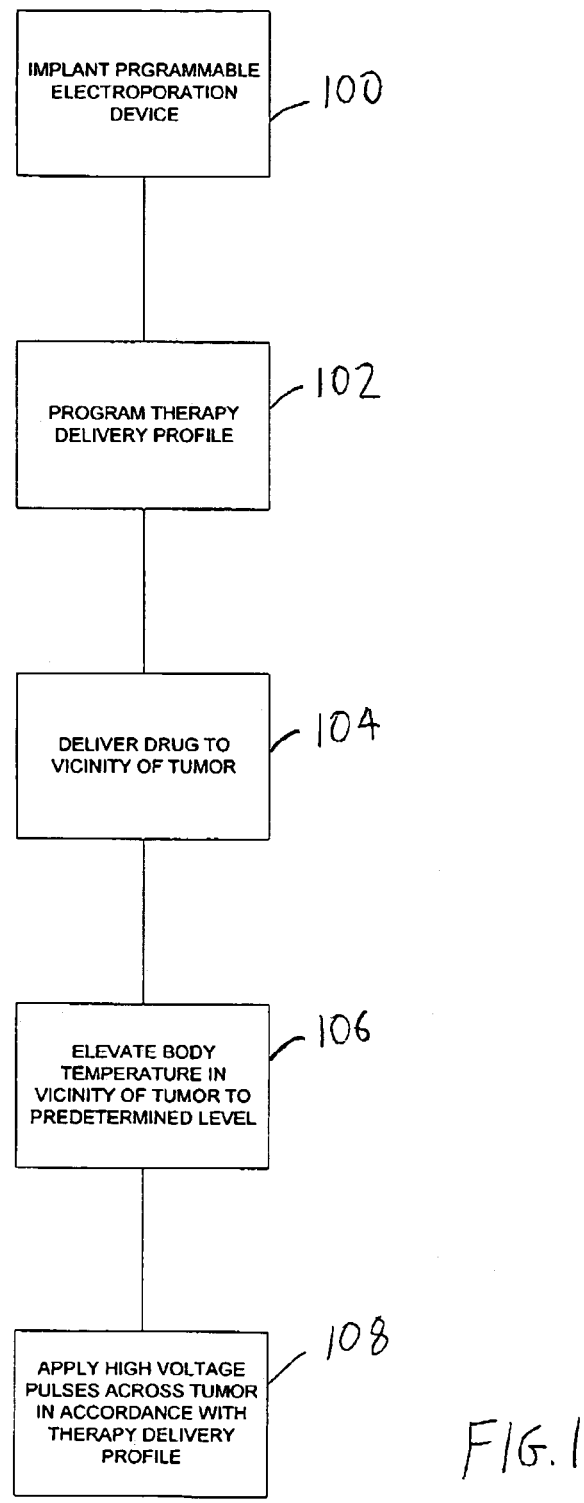
FIG. 1 is a flow chart illustrating an electroporation cancer treatment method in accordance with one embodiment of the invention.

FIG. 1 illustrates a method of treating cancer in accordance with one exemplary embodiment of the invention. In general, a programmable, wholly implantable medical device (IMD) in accordance with the present invention is implanted at 100. The IMD is operable to deliver electroporation therapy as further described below. A therapy profile defining drug delivery and electroporation parameters may be programmed into the IMD at 202 either prior to or after implantation. A chemotherapy drug is delivered (either locally or systemically) to the target tumor at 104. Optionally, the temperature of the tissue in and around the target tumor may be elevated at 106 to improve electroporation efficiency as further described below. Electroporation therapy, which includes one or more high voltage electrical pulses across the target tumor, may be initiated at 108 in accordance with the therapy profile programmed at 102.

While the electroporation apparatus and methods described herein are directed to cancer treatment, those of skill in the art will realize that they are adaptable for use in delivering most any substance to an intracellular target. For example, DNA transfer (e.g., for gene therapy or nucleic acid delivery) may benefit from the apparatus and methods described herein, as may techniques for delivering other (e.g., non-cancer treating) drugs.

Moreover, apparatus and methods of the present invention are not limited to any particular tissue. In fact, they may be used to treat most any cell or group of cells (e.g., soft tissue, bone, etc.) within a living organism.

Figure 2:
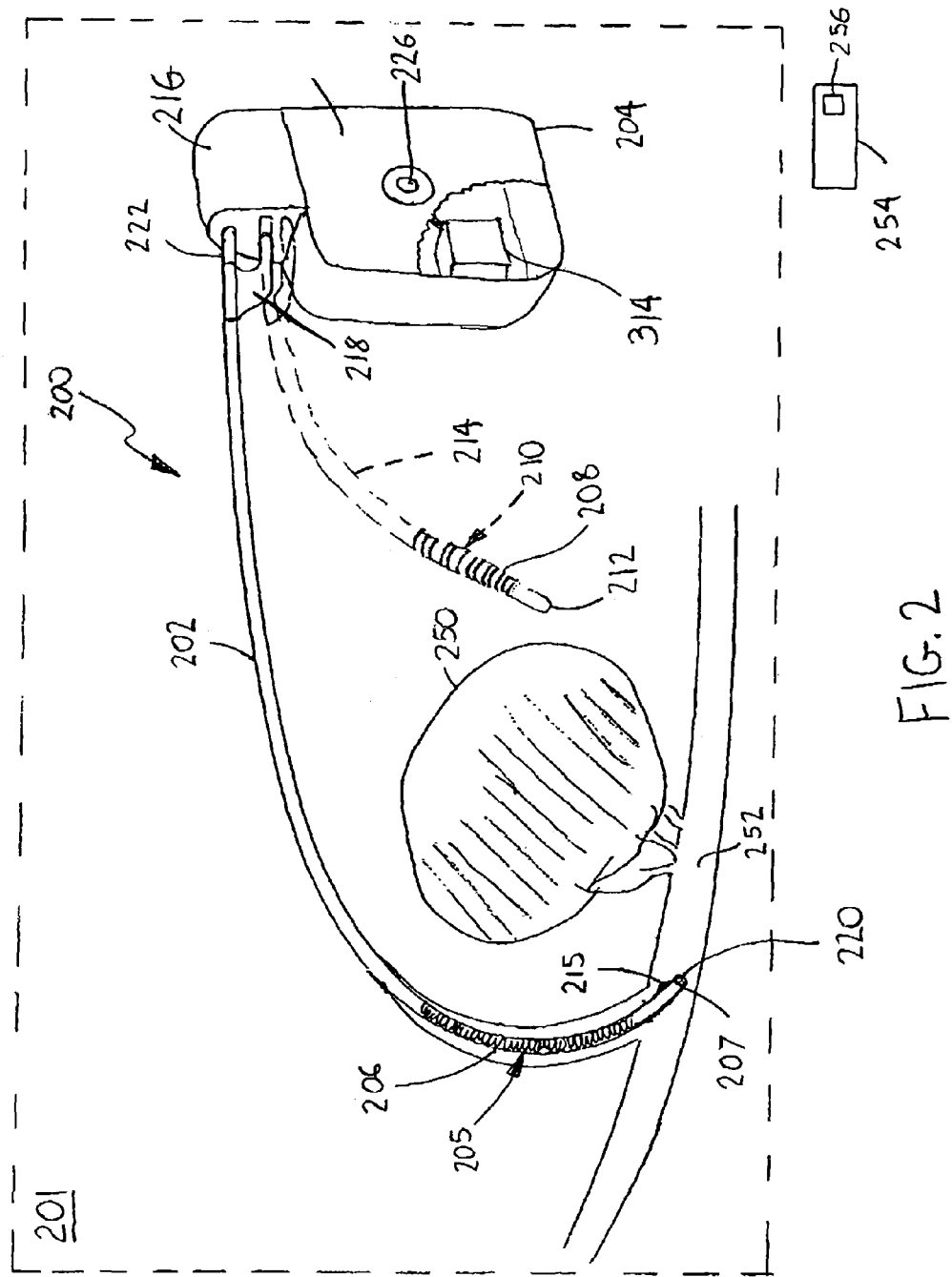
FIG. 2 is an implantable medical device (IMD) for electroporation cancer treatment in accordance with one embodiment of the invention, wherein the IMD is shown implanted within a body of a patient.

FIG. 2 is a simplified schematic view of one embodiment of implantable medical device 200 in accordance with the present invention. IMD 200 shown in FIG. 2 is a wholly implantable electroporation cancer treatment device having at least first lead 202 attached to hermetically sealed enclosure or housing 204. IMD 200, as further described below, may be implanted near cancerous tumor 250 wholly within human or mammalian body 201.

First lead 202 may be most any length and preferably includes an elongate insulated lead body carrying at least one first electrode 205, which may be concentrically wound, for delivering therapy as further described below, in an embodiment, first lead 202 may be wholly implantable. Preferably, first electrode 205 includes high voltage first coil 206 located near distal end 207 of first lead 202. First electrode 205 may be separated from other components of first lead 202 by tubular insulative sheaths (not shown). High voltage first coil 206 and/or first electrode 205 may be fabricated from platinum, platinum alloy or other materials known to be usable in implantable electrodes.

While first lead 202 is specialized in its adaptation for electroporation cancer treatment, it may be similar in many respects to implantable cardiac pacing leads such as those discussed in U.S. Pat. Nos. 5,099,838 and 5,314,430 to Bardy. Most any other lead configuration may also be practiced in conjunction with the present invention.

High voltage first coil 206 is operable to provide a series of high voltage electrical pulses across tissue of tumor 250. The electroporation therapy electrical field may be formed between first coil 206 and a conductive portion of housing 204 or, alternatively, between first coil 206 and optional, high voltage second coil 208 of second electrode 210 which may be located at distal end 212 of second lead 214 in a manner similar to that described with respect to first lead 202. For example, first coil 206 and second coil 208 may be similar in many respects to coils now used for tachycardia therapy delivery.

Where second electrode 210 is utilized, housing 204 may be electrically insulated by using a plastic coating such as parylene or silicone rubber. Where second electrode 210 is not used, a portion of housing 204 may be made from a conductive material, e.g. titanium, and left uninsulated. Alternatively, some other division between insulated and uninsulated portions of the housing 204 may be employed. The uninsulated portion of housing 204 may then serve as a subcutaneous electrode for the formation of the electroporation electric field.

IMD 200 may be programmed, either before or, more preferably, after, implantation via external programming device or apparatus 254. Programming device 254 may include telemetry circuitry 256 to permit wireless communication with logic and control circuitry of IMD 200 as is generally known in the art. In an embodiment, the logic and control circuitry may be contained within housing 204.

Devices and methods of the present invention thus permit an implantable electroporation system operable to treat a wide range of tumors at most any location within the body. Moreover, because these devices are generally self-contained, therapy does not require external equipment to electroporate the tumor site. As further described below, some embodiments of the invention may also control drug delivery, thereby permitting preprogrammed therapy to occur at most any time.

With this introduction, specific embodiments of apparatus and methods of treating cancer in accordance with the present invention will now be described. These embodiments are exemplary only and other embodiments are certainly possible without departing from the scope of the invention.

In the exemplary IMD 200 illustrated in FIG. 2, first lead 202 is threaded through blood vessels as known in the art until distal end 207 is in (or proximate) vessel 252 which provides blood supply to tumor 250. Alternatively, first lead 202 (and other leads discussed herein) may be punctured through the soft tissues in and around tumor 250. Housing 204 is preferably implanted at a location on a side of tumor 250 opposite first electrode 205. Alternatively, as mentioned above, second lead 214 may be provided and located such that second electrode 210 is at a location on a side of the tumor 250 opposite first electrode 205. For reasons that will become apparent, distal end 207 of first lead 202 preferably includes a sensor operable to detect a biological parameter. For example, temperature sensor 215 capable of detecting tissue and/or blood temperature near tumor 250 may be provided. As explained more fully below temperature sensor 215 may provide a feedback, e.g., a sense, signal which at least partially controls the electroporation therapy delivered by IMD 200.

Housing 204 includes connector module or header 216. Header 216 preferably permits coupling of first lead 202 to housing 204. That is, header 216 permits coupling of electrical connector 218 of first lead 202 to is housing 204.

First lead 202 may also incorporate drug catheter 220 for delivering a chemotherapy drug from reservoir 314 of wholly implantable medical device 200 to distal end 207. To accommodate catheter connection, the connector at the proximal end of first lead 202 may be bifurcated into electrical connector 218 and catheter port 222, both of which may couple to header 216. Catheter port 222 allows interconnection of drug reservoir 314 to catheter 220. Housing 204 may include refill valve 226 to permit filling and refilling of drug reservoir 314 contained within housing 204.

Figure 3:
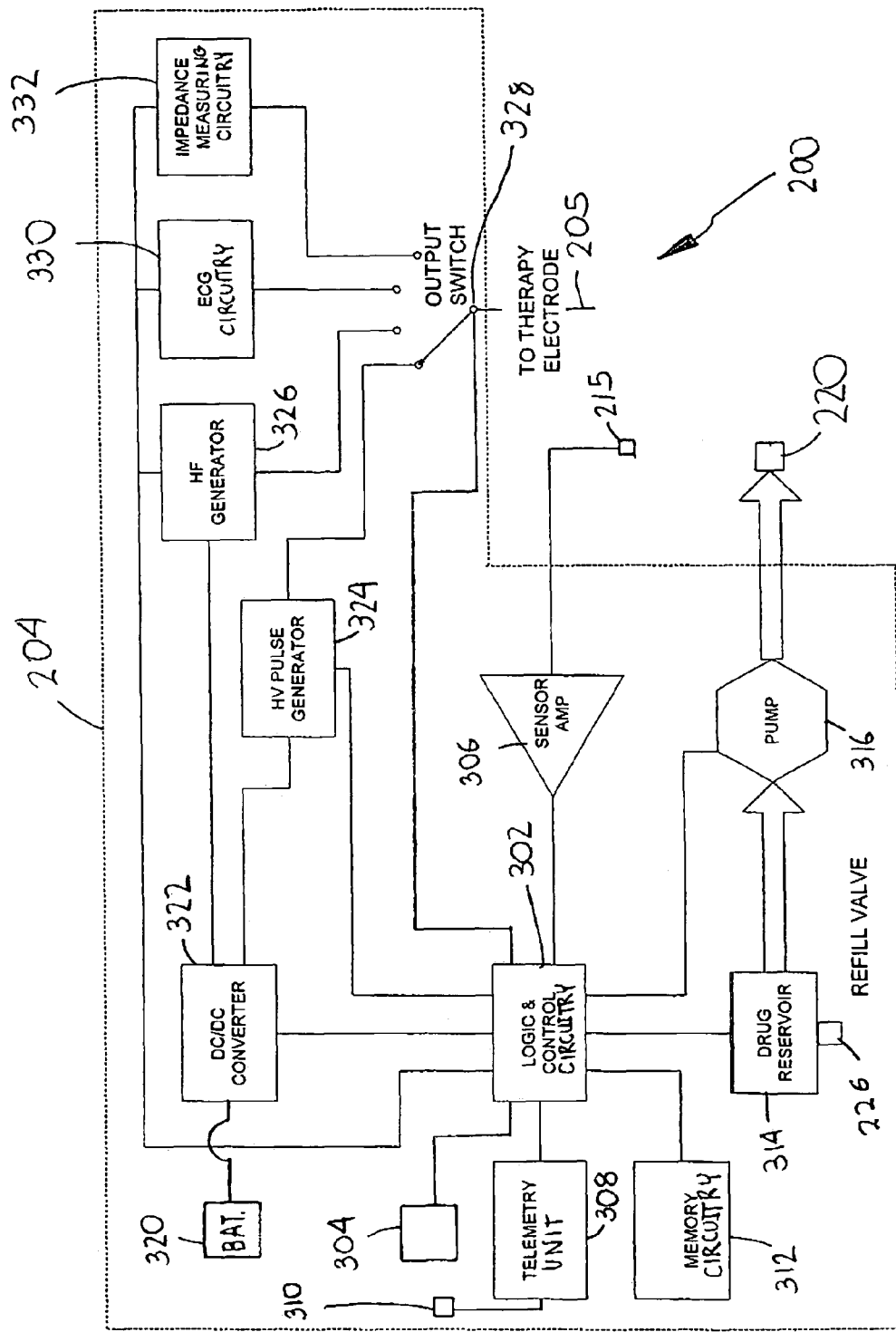
FIG. 3 is a functional block diagram of the IMD of FIG. 2 in accordance with one embodiment of the present invention.

FIG. 3 is a block diagram illustrating the constituent components of IMD 200 in accordance with one embodiment of the present invention. IMD 200 is shown as including logic and operative control circuitry 302, which is preferably coupled to microcomputer circuit 304. Sensor circuitry, e.g., sensor amp 306, typically (although not necessarily) provides a sensor input, in an embodiment a biological parameter, to logic and operative control circuitry 302 that varies as a function of a measured parameter relating to the patient's condition. For example, sensor amp 306 may be coupled to temperature sensor 215 and calibrated to provide a temperature signal to logic and operative control circuitry 302. Sensor amp 306 may couple to sensor 215 via electrical connector 218 (see FIG. 2).

While shown as utilizing microcomputer circuit 304, other embodiments of IMD 200 may be implemented utilizing logic circuitry.

Microcomputer circuit 304 may be an interrupt driven device responsive to interrupts from the various sensors and other circuitry associated with IMD 200. Microcomputer circuit 304 preferably includes, or is at least coupled to, a microprocessor, a system clock, and RAM/ROM components. Microcomputer circuit 304 may additionally include a custom integrated circuit (IC) to best implement the control and recording aspects of IMD 200. While illustrated as a separate component, microprocessor circuit 304 may be combined with other circuits, e.g., logic and control circuitry 302, telemetry circuitry, etc., onto a single IC.

IMD 200 in FIG. 3 is preferably programmable by means of programming device 254 (see FIG. 2). IMD 200 preferably includes telemetry circuitry which may include, for example, both telemetry unit 308 and antenna 310. The telemetry circuitry is preferably operable to permit bi-directional RF communication, e.g., transmitting and receiving, with programming device 254. That is, antenna 310 and telemetry unit 308 permit uplink/downlink telemetry with programming device 254.

By way of example, telemetry unit 308 may be similar to that disclosed in U.S. Pat. No. 4,556,063 issued to Thompson et al., or to that disclosed in U.S. Pat. No. 5,354,319 issued to Wyborny et al. It is generally preferred that the particular programming and telemetry scheme selected permit the entry and storage of cancer therapy parameters. The specific embodiments of antenna 310 and telemetry unit 308 presented herein are shown for illustrative purposes only, and are not intended to limit the scope of the invention in any way.

Programming device 254 may include a programmer similar in many respects to commercially available cardiac programmers such as the Medtronic Model 9790 programmer, which is microprocessor-based and provides a series of encoded signals to the subject IMD. Typically, a programming wand or head which transmits or telemeters radio-frequency (RF) encoded signals is utlized. Such a telemetry system is described in U.S. Pat. No. 5,354,319 to Wyborny et al.

The programming methodology disclosed in Wyborny et al.'s '319 patent is identified herein for illustrative purposes only. Any of a number of suitable programming and telemetry methodologies known in the art may be employed so long as the desired information is transmitted to and from IMD 200.

Memory circuitry 312 may be provided to enable storage of information regarding various functions of IMD 200. Preferably, memory circuitry 312 stores relevant diagnostic parameters and other information that may be interrogated by programming device 254 to evaluate the status of IMD 200.

Drug reservoir 314 shown in FIG. 3 is coupled to catheter port 222 (see FIG. 2) by pump 316. As further explained below, pump 316, under control of logic and control circuitry 302, may deliver the chemotherapy drug from drug reservoir 314 to catheter 220 via drug delivery catheter port 222 (see FIG. 2). Logic and control circuitry preferably monitors the volume of reservoir 314. When necessary, reservoir 314 may be refilled via valve 226. Refilling may be achieved, for example, by locating housing 204 such that valve 314 is at or near the surface of the skin. Alternatively, valve 314 may be accessed by a subcutaneously placed catheter or hypodermic needle.

Electrical components shown in FIG. 3 are powered by an appropriate implantable battery power source 320 in accordance with common practice in the art. For the sake of clarity, the coupling of battery power to the various components of IMD 200 may not be shown in the Figures.

A current converter, e.g., direct current to direct current (DC/DC) converter 322, is preferably coupled to an energy source, e.g., a battery source 320. DC/DC converter 322 is preferably capable of converting the voltage of battery source 320 to the levels necessary for effective cancer treatment. For example, DC/DC converter 322 is shown connected to electrical pulse generator, e.g., high voltage (HV) pulse generator 324. HV pulse generator 324 may be similar in most respects to HV pulse generators known for use with implantable cardioverters utilizing charged capacitors. As discussed in more detail below, HV pulse generator 324 is operable to produce the high voltage pulses necessary for electroporation therapy.

IMD 200 shown in FIG. 3 may also include high frequency (HF) generator 326 similar in many respects to that described in U.S. Pat. No. 5,386,837 to Sterzer but preferably having higher power output. HF generator 326 may apply a high frequency stimulus to target tissue as further described below. Application of such high frequency stimulation may beneficially produce an elevated temperature in the target tissue or the area around the target tissue.

Either HV pulse generator 324 or HF generator 326 may be coupled to first electrode 205 by output switch 328 which is under control of logic and control circuitry 302. In addition, output switch 328 may be selectively coupled to electrocardiogram (ECG) circuitry 330 or impedance measuring circuitry 332.

When output switch 328 is connected to ECG circuitry 330, an electrocardiogram of the heart may be measured between first electrode 205 and housing 204 (or between first electrode 205 and second electrode 210). ECG circuitry 330 may then detect a qRs complex of the patient's electrocardiogram. For reasons further explained below, qRs complex may be utilized to improve various aspects of the electroporation therapy.

When output switch 328 is connected to impedance measuring circuitry 332, electrical impedance between first electrode 205 and housing 204 (or second electrode 210) may be measured. Impedance measurements may be used to suspend or adjust therapy delivery in the event edema is detected as further described below.

Figure 4:
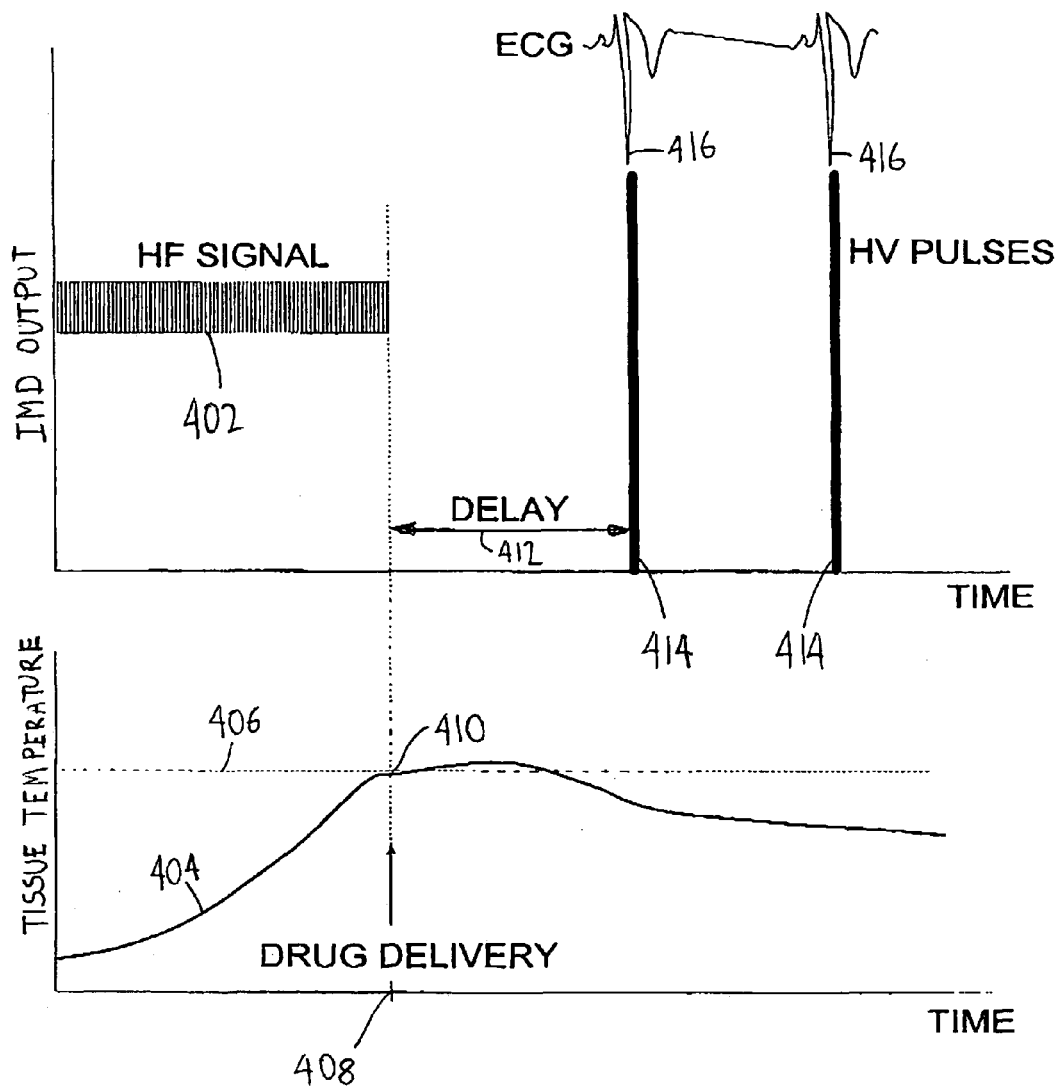
FIG. 4 is an exemplary timing diagram for the IMD of FIGS. 2 and 3.

FIG. 4 illustrates an exemplary therapy delivery timing diagram for IMD 200 of FIGS. 2 and 3. In particular, FIG. 4 illustrates both IMD 200 output and tissue temperature as a function of time. In describing FIG. 4, frequent reference is made to the components of IMD 200 illustrated in FIGS. 2 and 3.

Therapy delivery may be initiated by application of HF stimulus 402. For example, first electrode 205 of IMD 200 may be coupled via output switch 328 to HF generator 326 (see FIG. 3). HF generator 326 may then cause a portion of the first electrode 205 to produce a high frequency, low amplitude stimulus, e.g., a vibration having a frequency of about 100 kHz to about 5 MHz and an amplitude of about 20 Volts (V) to about 200 V (as used herein, "high frequency" may include most any frequency ranging from about 100 kHz to about 1 GHz). This stimulus causes the temperature of the tissue and/or fluid in or around the tumor 250 (See FIG. 2) site to increase as illustrated by the temperature profile 404. Temperature may be monitored periodically or continuously via temperature sensor 215 (see FIGS. 2 and 3) and sensor amp 306.

Once local temperature reaches a preprogrammed threshold therapy temperature (Tth) 406 at time 408, logic and control circuitry 302 may terminate HF stimulus 402. Delivery of chemotherapy drugs may occur at 410 at or around the termination of HF stimulus 402, e.g., at or around time 408.

Before or after drug delivery at 410, output switch 328 may be connected to ECG circuitry 330 so that qRs complex may be detected during programmed delay interval 412. Once qRs complex is detected, output switch 328 may be connected to HV pulse generator 324. Alternatively, qRs complex may be detected at the end of delay interval 412 but prior to application of HV pulses.

At the completion of programmed delay interval 412, high voltage pulses 414 may be initiated. Preferably, pulses 414 are synchronized with the qRs complex previously determined by ECG circuitry 330. That is, HV pulses 414 are preferably delivered at or near qRs peak 416. Application of HV pulses 414 at qRs peak 416 may, among other advantages, avoid delivery of the HV pulses during potentially vulnerable periods of the cardiac cycle that could provoke arrhythmia.

HV pulses 414 may have most any electric field strength and pulse width that yield the desired electroporation characteristics. For example, electric field strengths of about 700 Volts/centimeter (V/cm) to about 1500 V/cm and pulse widths of about 50 microseconds to about 200 microseconds are possible. Moreover, while shown with only two pulses per therapy cycle in FIG. 4, the number of HV pulses 414 per cycle may vary depending on the programmed therapy profile. For example, about four to about eight pulses may constitute a sufficient electroporation cycle in many applications.

During application of HV pulses 414, cellular membranes of the tumor cells become sufficiently porous to permit entry of drug molecules. This process is further improved by the elevated temperature under which electroporation occurs (see FIG. 4).

After the programmed number of HV pulses 414 have occurred, output switch 328 (see FIG. 3) may optionally be connected to impedance measuring circuit 332. Impedance of the tissue between first electrode 205 and housing 204 (or between first electrode 205 and second electrode 210 of FIG. 2) may then be measured and compared to previously recorded impedance values. If the measured impedance value is less than the previously recorded impedance value, edema (the presence of abnormally large amounts of fluid in the intercellular tissue spaces) may be indicated. If edema is so indicated, the therapy cycle may be suspended until impedance is again detected to be within acceptable limits.

In conjunction with impedance detection and comparison, edema detection may also include temperature detection and comparison. For example, temperature sensor 215 may measure temperature and compare it to a previously measured value after HV pulse therapy. The temperature difference, along with impedance values, may then be analyzed by logic and control circuitry 302 to determine if edema is present.

Figure 5:
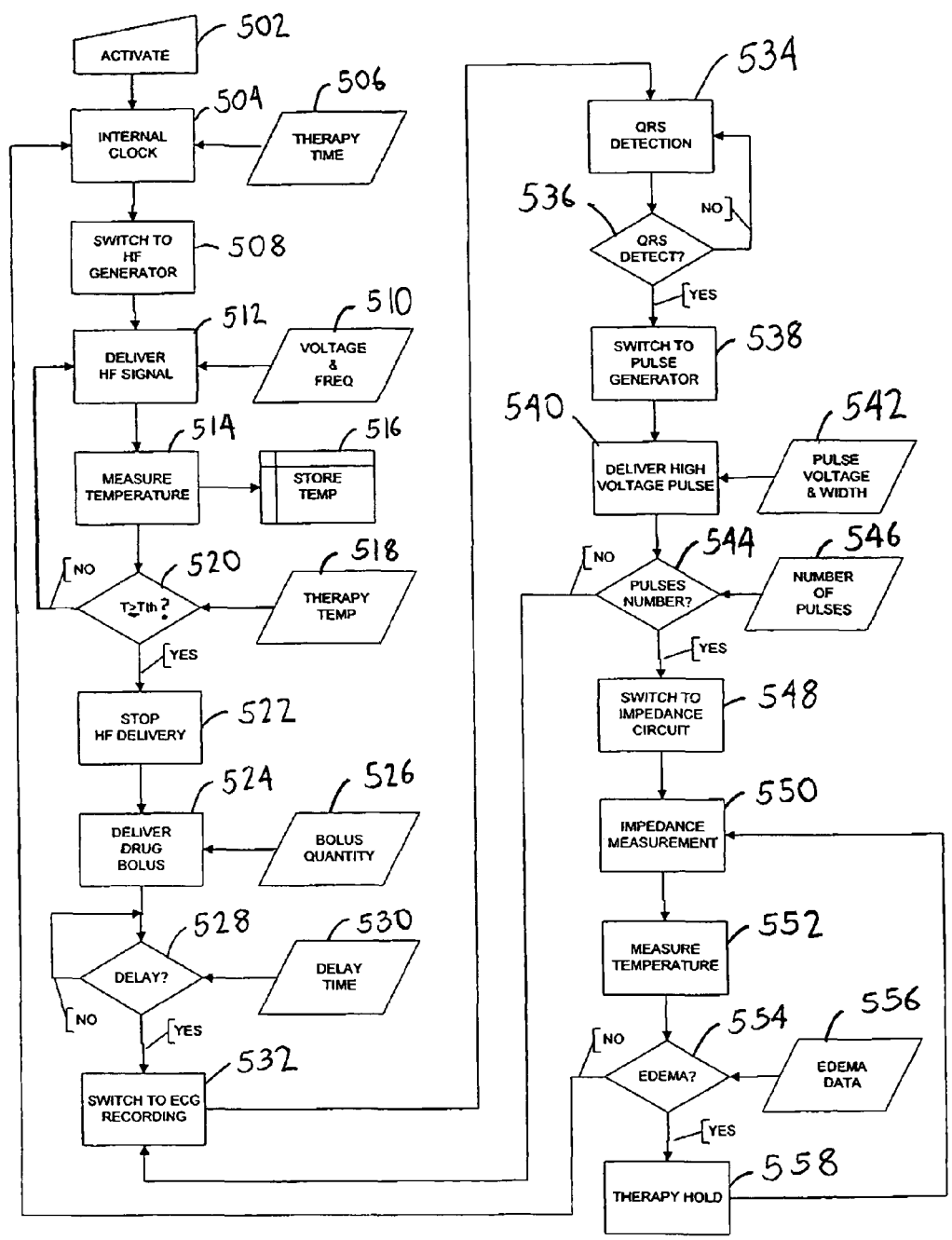
FIG. 5 is a functional block diagram illustrating an exemplary electroporation cancer treatment method utilizing the IMD of FIGS. 2-4.

FIG. 5 is a flow chart illustrating an exemplary method of electroporation treatment in accordance with the present invention. The method illustrated in FIG. 5 may utilize IMD 200 of FIGS. 2 and 3 operating as generally illustrated in FIG. 4. As a result, reference to FIGS. 2-4 is beneficial to a review of FIG. 5.

With IMD 200 successfully implanted, it may be programmed utilizing external programmer 254 (see FIG. 2). Alternatively, it may be programmed prior to implantation. Therapy may be activated at 502 by an external activation device similar to programmer 254 which may be held proximate IMD 200 to initiate therapy. Alternatively, therapy may be self-initiated by IMD 200 utilizing an internal clock at 504. That is, therapy initiation time may be programmed and stored in memory at 506 such that, at the prescribed time, therapy delivery is initiated.

Output switch 328 (see FIG. 3) may be coupled to HF generator 326 at 508. A programmed voltage and frequency stored in memory at 510 may then be input to logic and control circuitry 302 to produce the prescribed frequency and amplitude of the HF stimulus (see 402 of FIG. 4) at 512. Temperature is measured at periodic intervals at 514, e.g., by using temperature sensor 215, and the value (T) stored in memory at 516. The preprogrammed, prescribed therapy temperature (Tth) value is stored at 518 and each measured temperature value T is compared to Tth at 520. If T is equal to or greater than Tth, HF stimulation is terminated at 522. If T is less than Tth, then HF stimulation continues and control is returned to 512 as shown until T is equal to or greater than Tth.

After termination of the HF stimulus at 522, the prescribed quantity of cancer therapy bolus is delivered at 524. The bolus may be delivered from reservoir 314 to catheter 220 using pump 316 (see FIGS. 2 and 3). The prescribed quantity of drug bolus is controlled by logic and control circuitry 302 based upon a programmed quantity value stored at 526.

After bolus delivery at 524, a delay, such as that graphically illustrated at 412 in FIG. 4, occurs at 528. The delay terminates once the prescribed delay time, stored at 530, is reached.

Output switch 328 may then be coupled to ECG circuitry 330 at 532 and ECG recording may begin for purposes of qRs complex detection at 534. ECG circuitry 330 monitors ECG recordings until a qRs complex is detected at 536. Once qRs complex is so detected, output switch 328 may be coupled to HV pulse generator 324 at 538 and high voltage pulses (see 414 of FIG. 4) delivered at 540 based upon prescribed and programmed pulse characteristics, e.g., voltage pulse amplitude and duration, stored at 542. During this pulsing stage, electroporation of the cellular membranes occurs, permitting entry of the drug bolus into the cytoplasm of the tumor cells.

The number of HV pulses is compared at 544 to the preprogrammed number of pulses stored at 546. If the preprogrammed number of pulses has not been reached, control is returned to 532 as shown. Once the preprogrammed number of pulses is reached, HV pulsing may be terminated and the output switch 328 (see FIG. 3) may be coupled to impedance measuring circuitry 352 at 548. Impedance measurements may then be taken across the tumor tissue at 550 by using the first electrode 205 and the housing 204 (or the optional second electrode 210) as described above. Temperature measurements may also be taken at 552 using temperature sensor 215.

Impedance measurements and temperature measurements may be compared at 554 to edema data stored at 556. The edema data may include a threshold impedance value and preferably includes impedance information as a function of temperature such that a determination of edema may be made. The threshold impedance value may be preprogrammed or, alternatively, determined based upon impedance measurements taken before therapy.

If the measured impedance/temperature data is indicative of the presence of edema, e.g., if the measured impedance is less than the threshold impedance value, then therapy may be suspended at 558 and control returned to 550. The edema detection algorithm may then continue until edema is no longer detected at 554. At this point, control is returned to 504 and IMD 200 is ready for the next therapy delivery cycle.

Figure 6:
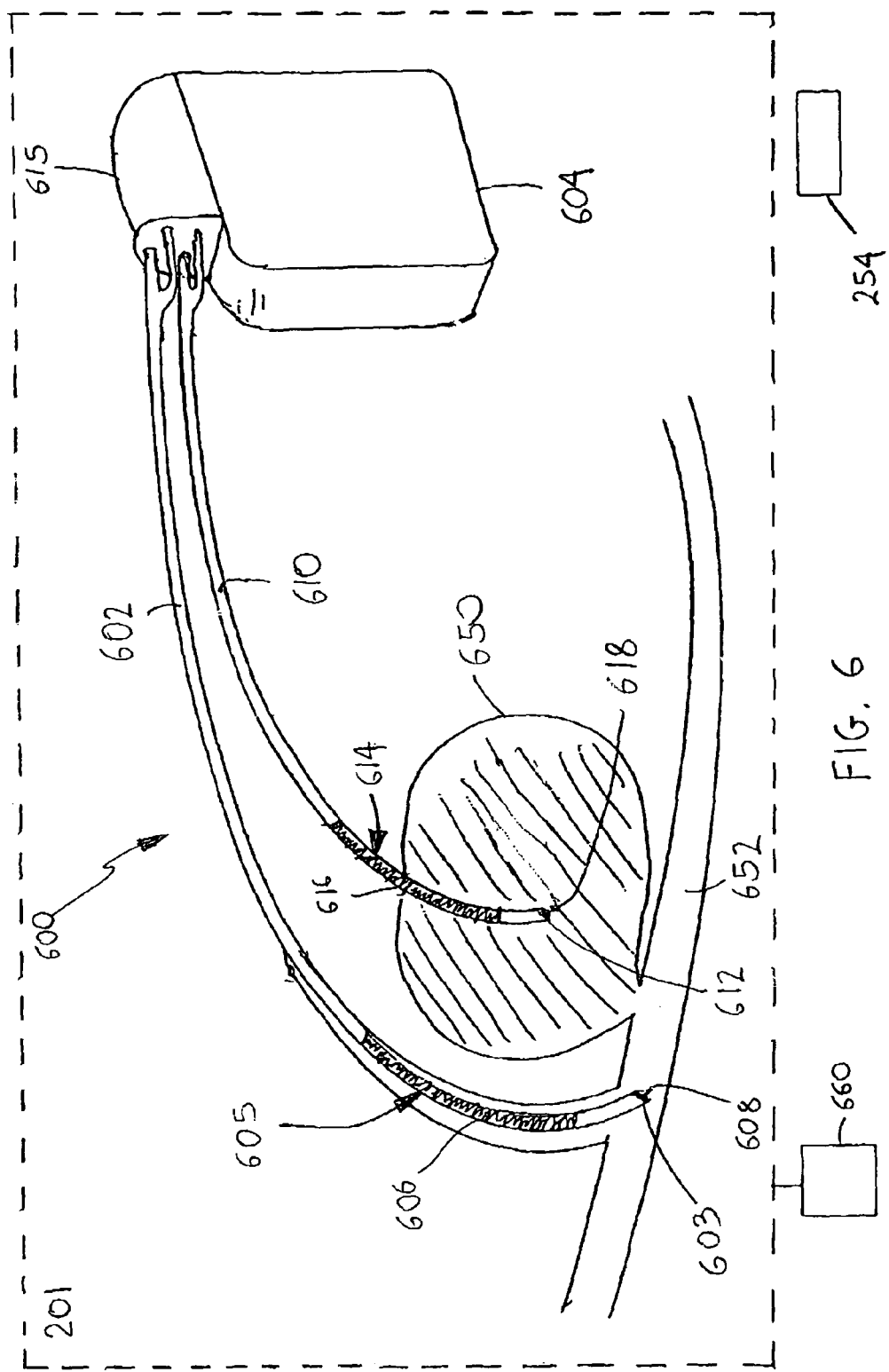
FIG. 6 is an IMD for electroporation cancer treatment in accordance with another embodiment of the invention.

FIG. 6 illustrates IMD 600 in accordance with another embodiment of the present invention as IMD 600 may be implanted into human or mammalian body 201. Like IMD 200, IMD 600 includes first lead 602 extending from header 615 of housing 604. Header 615, like header 215 described above with reference to FIG. 2, may include multiple conductors and/or ports to permit coupling with at least first lead 602.

Distal end 603 of first lead 602 may be threaded through vessel 652 such that it is located proximate tumor 650. First electrode 605 for delivering therapy is located proximate distal end 603 of first lead 602. First electrode 605 may include high voltage first coil 606 similar in most respects to HV first coil 206 discussed above. A biological sensor, e.g., drug concentration sensor 608, operable to detect the concentration of a cancer therapy drug may be located near distal end 603 of first lead 602.

IMD 600 preferably also includes second lead 610 having, like first lead 602, distal end 612 and second electrode 614 for delivering therapy located proximate thereto. Second electrode 614 preferably includes HV second coil 616 similar in most respects to HV first coil 606. Temperature sensor 618 may be provided and located at or near distal end 612 of second lead 610.

Leads 602 and 610 are structurally similar in most respects to lead 202 described above with the exception that leads 602, 610 exclude a catheter. Preferably, housing 604 is electrically inactive in the configuration of FIG. 6.

Distal end 612 of second lead 610 is preferably implanted directly into tumor 650 as shown in FIG. 6. However, other embodiments wherein distal end 612 is located externally but proximate tumor 650 are also within the scope of the invention.

Figure 7:
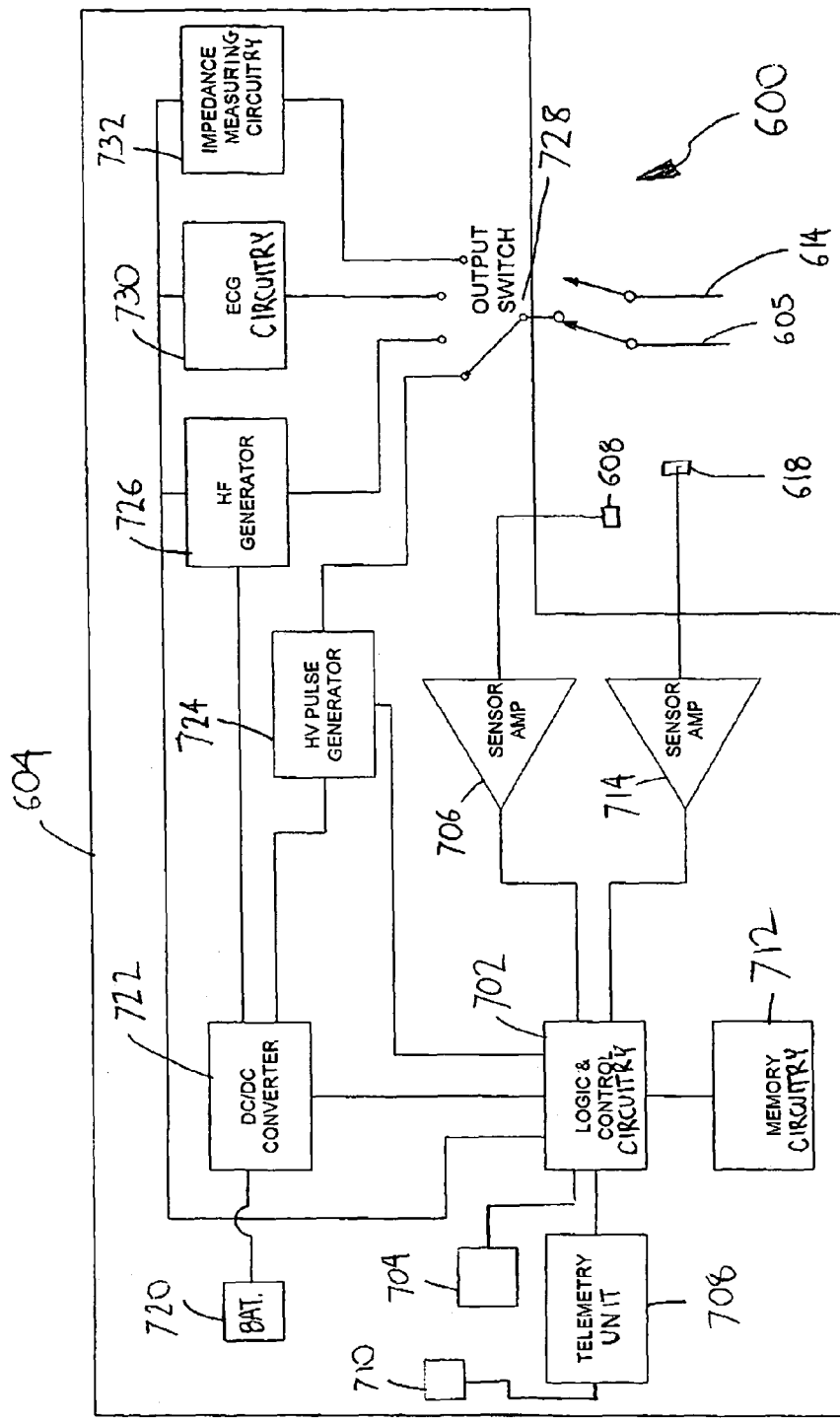
FIG. 7 is a functional block diagram of the IMD of FIG. 6 in accordance with one embodiment of the present invention.

FIG. 7 is a block diagram illustrating the constituent components of IMD 600 in accordance with one embodiment of the present invention.

IMD 600 is shown as including logic and control circuitry 702 coupled to microcomputer circuit 704. Sensor circuitry may include both first sensor amp 706 and second sensor amp 714. First sensor amp 706 provides a sensor input. e.g., a feedback input, to logic and control circuitry 702 that varies as a function of a measured parameter relating to the patient's condition. For example, first sensor amp 706 may be coupled to drug concentration sensor 608 (see FIG. 6) located at distal end 603 of first lead 602. As a result, first sensor amp 706 may be calibrated to provide a drug concentration signal to logic and control circuitry 702.

Second sensor amp 714 may provide a second sensor input to logic and control circuitry 702 that varies as a second function of a measured parameter relating to the patient's condition. For example, sensor amp 714 may be coupled to temperature sensor 618 (see FIG. 6) located at distal end 612 of second lead 610. As a result, second sensor amp 714 may be calibrated to provide a temperature signal to logic and control circuitry 702.

IMD 600 is preferably programmable by means of programming device 254 (see FIG. 6) as generally described above with reference to IMD 200. IMD 600 thus includes telemetry circuitry, which may include telemetry unit 708 and antenna 710, operable to communicate with programming device 254, e.g., antenna 710 is connected to telemetry unit 708 to permit uplink/downlink telemetry with programmer 254.

Once again, it is generally preferred that the particular programming and telemetry scheme selected permit the entry and storage of cancer therapy parameters. The specific embodiments of antenna 710 and telemetry unit 708 presented herein are shown for illustrative purposes only, and are not intended to limit the scope of the present invention. Any of a number of suitable programming and telemetry methodologies known in the art may be employed so long as the desired information is transmitted to and from IMD 600.

Memory circuitry 712 may be provided to enable storage of various information of IMD 600. Preferably, memory circuitry 712 stores relevant diagnostic parameters as well as therapy data. Memory circuitry 712 may be interrogated by programming device 254 to evaluate the status of IMD 600 and to reprogram therapy profiles.

Electrical components shown in FIG. 7 are powered by an appropriate implantable energy source, e.g., battery power source 720, in accordance with common practice in the art. For the sake of clarity, the coupling of battery power to the various components of IMD 600 may not be shown in the Figures.

DC/DC converter 722 is preferably coupled to battery source 720 and is capable of converting the voltage of battery source 720 to the levels necessary for effective cancer treatment. For example, DC/DC converter 720 is shown connected to high voltage (HV) pulse generator 724. Like HV pulse generator 324 discussed above, HV pulse generator 724 is operable to produce the high voltage pulses necessary for electroporation therapy.

IMD 600 shown in FIGS. 6 and 7 may also include high frequency (HF) generator 726. HF generator 726 may apply a high frequency stimulus to target tissue as described above with reference to HF generator 326 (see FIG. 3). Application of such high frequency stimulation may beneficially produce an elevated temperature in or around the target tissue.

Either the HV pulse generator 724 or the HF generator 726 may be coupled to either or both the first electrode 605 or second electrode 614 by output switch 728 which is under control of logic and control circuitry 702. In addition, output switch 728 may be connected to electrocardiogram (ECG) circuitry 730 or impedance measuring circuitry 732.

When output switch 728 is connected to ECG circuitry 730, first electrode 605 may be used to measure the electrical activity of the heart. ECG circuitry 730 may then determine qRs complex based on these measurements. For reasons described elsewhere herein, qRs complex may be utilized to improve aspects of the electroporation therapy.

When output switch 728 is connected to impedance measuring circuitry 732, electrical impedance between first electrode 605 and second electrode 614 may be measured Alternatively, impedance may be measured between either first electrode 605 and housing 604 or second electrode 614 and housing 604.

As a result, it is apparent that IMD 600 shares many similar components, e.g., HV pulse generator 724, HF generator 726, ECG circuitry 730, and impedance measuring circuitry 732, with IMD 200 already described herein.

Figure 8:
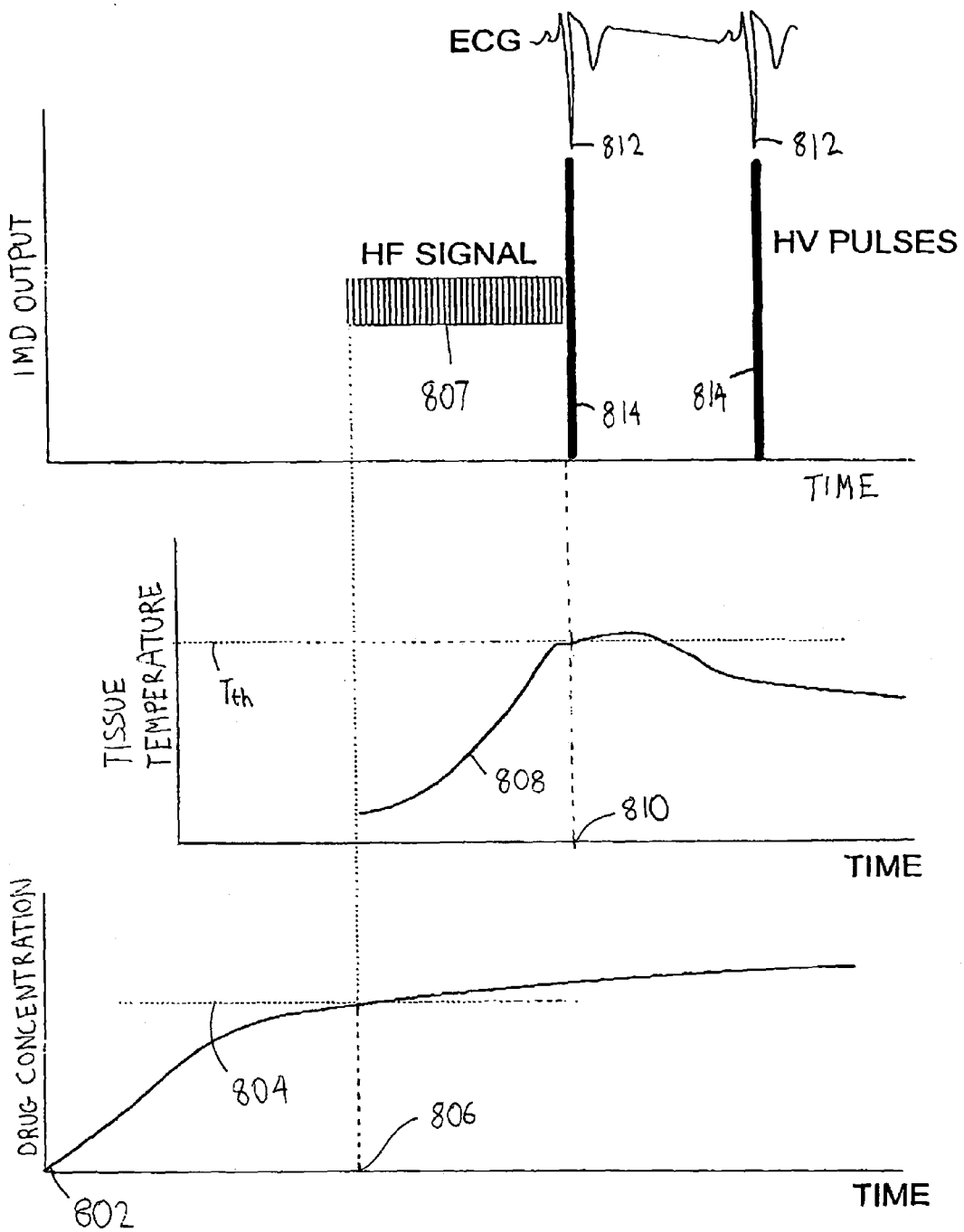
FIG. 8 is an exemplary timing diagram for the IMD of FIGS. 6 and 7.

FIG. 8 illustrates an exemplary therapy delivery timing diagram for IMD 600 of FIGS. 6 and 7. In particular, FIG. 8 illustrates IMD output, tissue temperature, and drug concentration as a function of time. In describing FIG. 8, frequent reference is made to the components of IMD 600 illustrated in FIGS. 6 and 7. As a result, reference to FIGS. 6 and 7 is useful in understanding FIG. 8.

Therapy may be initiated by introduction of the chemotherapy drug at 802. Unlike IMD 200, IMD 600 may utilize an independent drug delivery apparatus and methodology. For example, chemotherapy drugs may be delivered intravenously (either locally or systemically) via a syringe or an external infusion pump 660 (see FIG. 6) as known in the art.

Drug concentration near tumor 650 may be monitored by drug concentration measurement sensor 608 (see FIG. 6). Once the drug concentration reaches a predetermined level 804 at time 806, application of HF stimulus 807 may occur. For example, one or both of first electrode 605 and second electrode 614 of IMD 600 (see FIG. 6) may be coupled via output switch 728 to HF generator 726 (see FIG. 7). HF generator 726 may then cause a high frequency signal between first electrode 605 and second electrode 614 (or housing 604) to produce high frequency stimulus 807. Stimulus 807 causes the temperature of the tissue in or around tumor 650 (See FIG. 6) to increase as illustrated by the temperature profile 808. Temperature may be monitored periodically or continuously via temperature sensor 618 (see FIGS. 6 and 7) and sensor amp 714.

Temperature at tumor 650 eventually reaches a preprogrammed threshold therapy temperature (Tth) as shown at time 810. At time 810, or shortly thereafter, logic and control circuitry 702 may terminate HF stimulus 807. At some point prior to application of HF stimulus or shortly thereafter, output switch 728 may be connected to ECG circuitry 730 for purposes of qRs complex detection.

Once qRs complex is detected, output switch 728 may be connected to HV pulse generator 724 (see FIG. 7) and high voltage pulses 814 may be initiated. Preferably, pulses 814 are synchronized with qRs peaks 812 as shown in FIG. 8. That is, one or more HV pulses 814 are preferably delivered at or near qRs peak 812 during the cardiac cycle.

Like the previous embodiments, HV pulses 814 may be of most any amplitude, electric field strength, width, and number that yield acceptable electroporation results. For example, electric field strengths of about 700 V/cm to about 1500 V/cm and pulse widths of about 50 microseconds to about 200 microseconds are possible. Moreover, while the number of HV pulses 814 may vary, about four to about eight pulses may be sufficient in many applications for successful electroporation therapy.

After the programmed number of HV pulses 814 have occurred, output switch 728 (see FIG. 7) may optionally be connected to impedance measuring circuit 732. Impedance of the tissue between first electrode 605 and second electrode 614 (or between either electrode 605, 614 and housing 604) may be measured and compared to previously recorded impedance values. If the measured impedance value is less than the previously recorded impedance value, edema may be indicated. If edema is so indicated, the therapy cycle may be suspended until impedance is again within acceptable limits.

In conjunction with impedance detection and comparison, edema detection may also include temperature detection and comparison. For example, temperature sensor 618 may measure temperature and compare it to a previously measured value taken before therapy began. The temperature difference, along with impedance values, may then be analyzed by to determine if edema is present.

Figure 9:
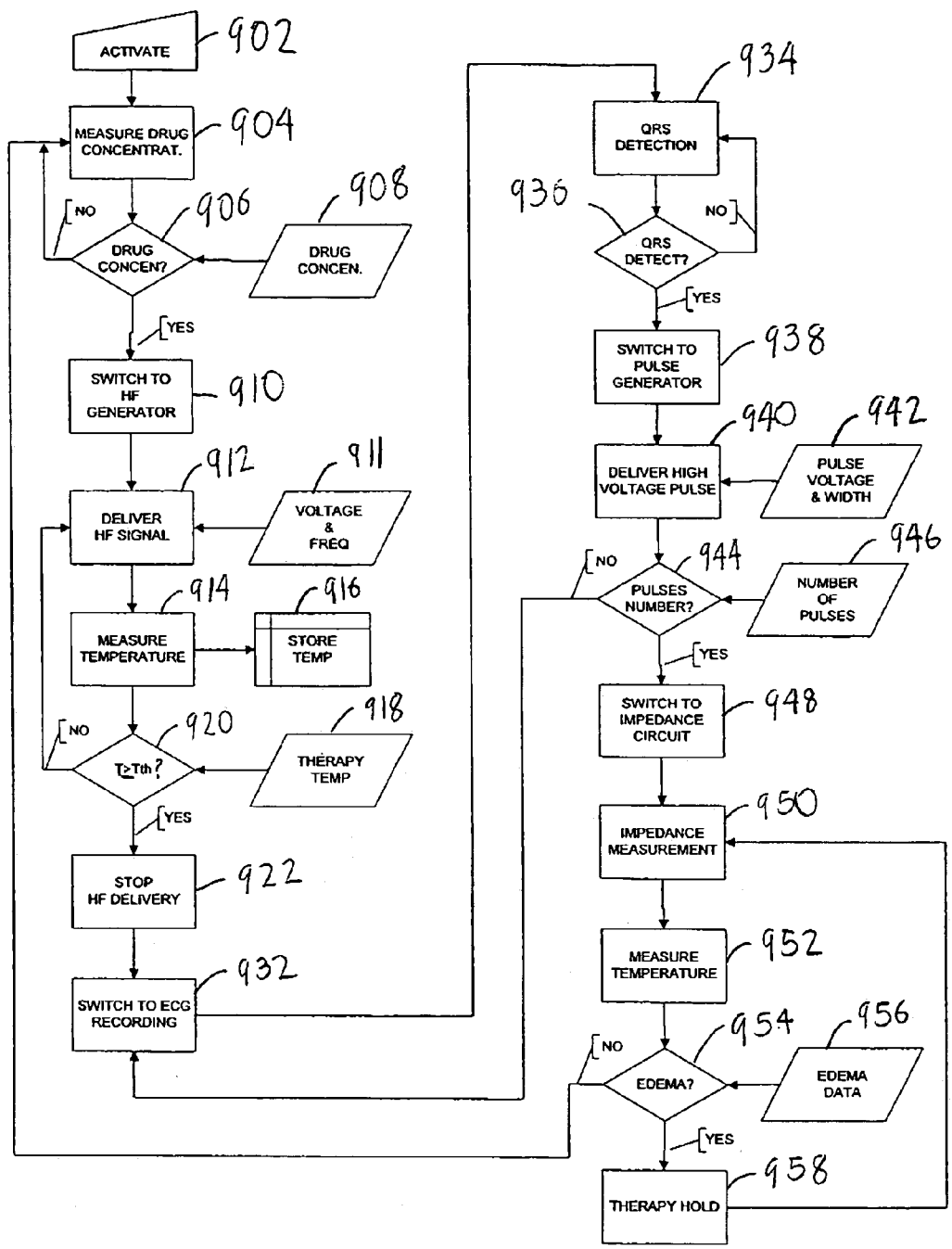
FIG. 9 is a functional block diagram illustrating an exemplary electroporation cancer treatment method utilizing the IMD of FIGS. 6-8.

FIG. 9 is a flow chart illustrating an exemplary method of electroporation treatment in accordance with another embodiment of the present invention. The method illustrated in FIG. 9 may utilize IMD 600 of FIGS. 6 and 7 operating in a manner similar to that illustrated in FIG. 8. As a result, frequent reference to these previous figures is beneficial to an understanding of the method illustrated in FIG. 9.

Activation at 902 may be initiated by an external device similar to programmer 254 which may be held proximate IMD 600. Alternatively, therapy may be self-initiated by IMD 600, e.g., therapy may begin once a threshold drug concentration level is detected.

Once drug concentration is measured at 904, the measured value may be compared at 906 to a prescribed value stored at 908. Drug concentration is preferably detected by drug concentration measurement sensor 608 (see FIG. 6).

If the measured value is too low, control returns to 904 and the measurement cycle continues. If measured drug concentration is equal to or in excess of the prescribed value, output switch 728 (see FIG. 7) may be connected to HF generator 726 as illustrated at 910 in FIG. 9. A programmed voltage and frequency stored in memory at 911 may then be input to logic and control circuitry 702 to produce the prescribed frequency and amplitude of the HF stimulus (see 807 in FIG. 8) at 912.

Temperature is preferably measured at periodic intervals at 914, e.g., by using temperature sensor 618 shown in FIGS. 6 and 7, and the value (T) stored in memory at 916. The prescribed therapy temperature (Tth) value is stored at 918 and each measured temperature value T is compared to Tth at 920. If T is equal to or greater than Tth, HF stimulation is terminated at 922. If T is less than Tth, then HF stimulation continues and control is returned to 912 as shown in FIG. 9 where temperature measurement continues until T is equal to or greater than Tth.

Output switch 728 may then be coupled to ECG circuitry 730 at 932 and ECG recording may begin for purposes of qRs complex detection at 934. ECG circuitry 930 continually monitors ECG recordings until a qRs complex is detected at 936. Once a qRs complex is so detected, output switch 728 may be coupled to HV pulse generator 724 at 938 and high voltage pulses (see 814 of FIG. 8) delivered at 940 based upon prescribed and programmed pulse characteristics, e.g., pulse voltage amplitude and duration, stored at 942.

After each pulse at 940, the number of applied HV pulses is compared at 944 to the preprogrammed number of pulses stored at 946. If the preprogrammed number of pulses has not been reached, control is returned to 932 as shown. Once the preprogrammed number of pulses is reached, HV pulsing may be terminated and the output switch 728 (see FIG. 7) may be coupled to impedance measuring circuitry 732 at 948. Impedance measurements may then be taken across the tumor tissue at 950 by using first electrode 605 and second electrode 614 (or either first electrode 605 or second electrode 614 and housing 604) as described above. Temperature measurements may also be taken at 952 using temperature sensor 618.

Impedance measurements and temperature measurements may be compared at 954 to threshold edema data stored at 956 in a manner similar to that described herein above, see e.g., FIG. 5. If the measured impedance/temperature data indicates edema is present, e.g., if the impedance is less than the threshold impedance value, then therapy may be suspended at 958 and control returned to 950 where the edema detection cycle may continue. Once edema is no longer detected at 954, control is returned to 904 and IMD 600 is ready for the next therapy cycle.

The method illustrated in FIG. 9 and elsewhere herein are, once again, exemplary only. Sequence steps may certainly be added (or removed) and the order of steps may be altered to address specific apparatus and therapy requirements.

Figure 10:
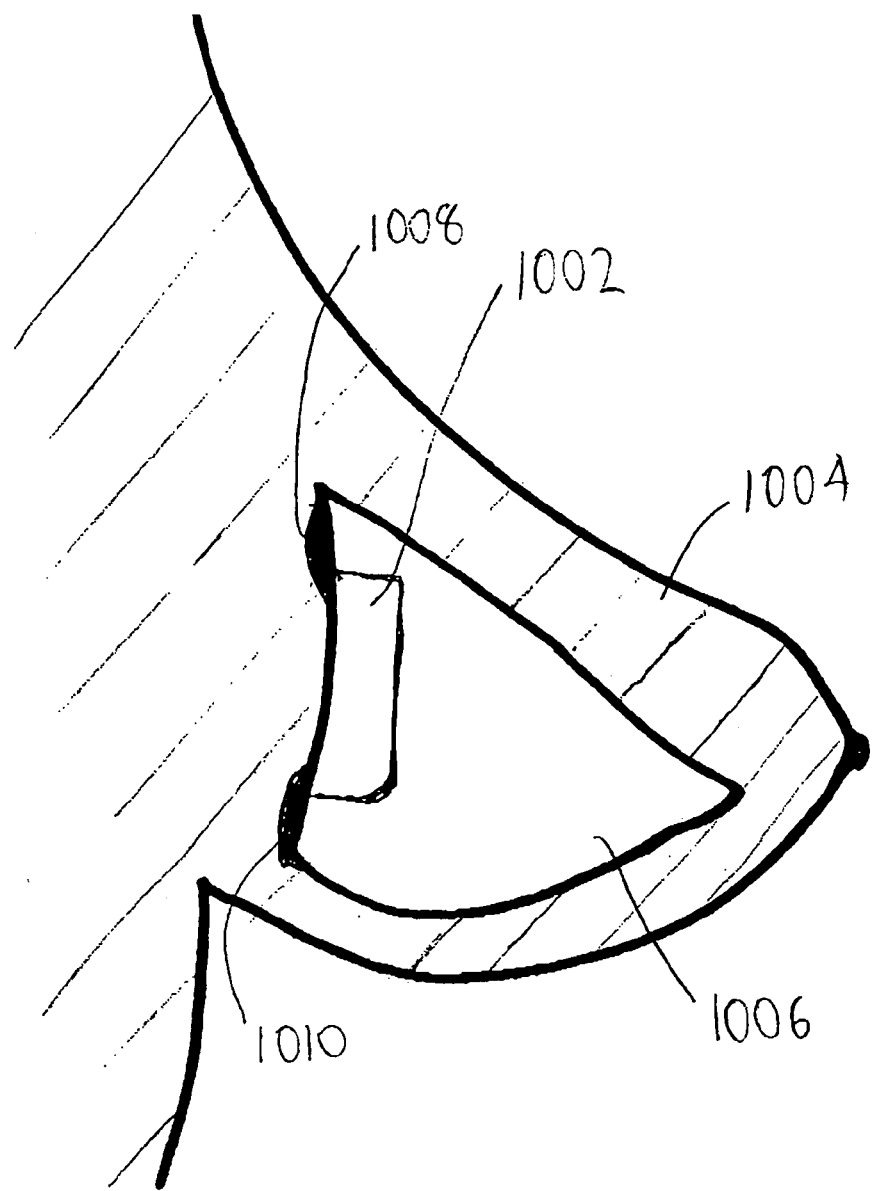
FIG. 10 is an exemplary application of electroporation cancer treatment in accordance with the present invention as it may be applied to treatment of breast carcinoma.

FIG. 10 illustrates an exemplary application of an apparatus and method in accordance with the present invention for treatment of breast carcinoma. In particular, FIG. 10 illustrates a cross sectional view of female breast 1004 after having undergone a partial mastectomy. IMD 1002, which may be configured as described in FIGS. 6-9, may be implanted either independently or as part of cosmetic implant 1006. IMD 1002 may include electrodes 1008 and 1010 which are similar in most respects to electrodes 605 and 614 described above with respect to FIG. 6. In accordance with the principles described herein above, electrodes 1008, 1010 may be used to deliver electroporation therapy to the remaining breast tissue by periodically applying high voltage electrical fields between electrodes 1008, 1010.

Figure 11:
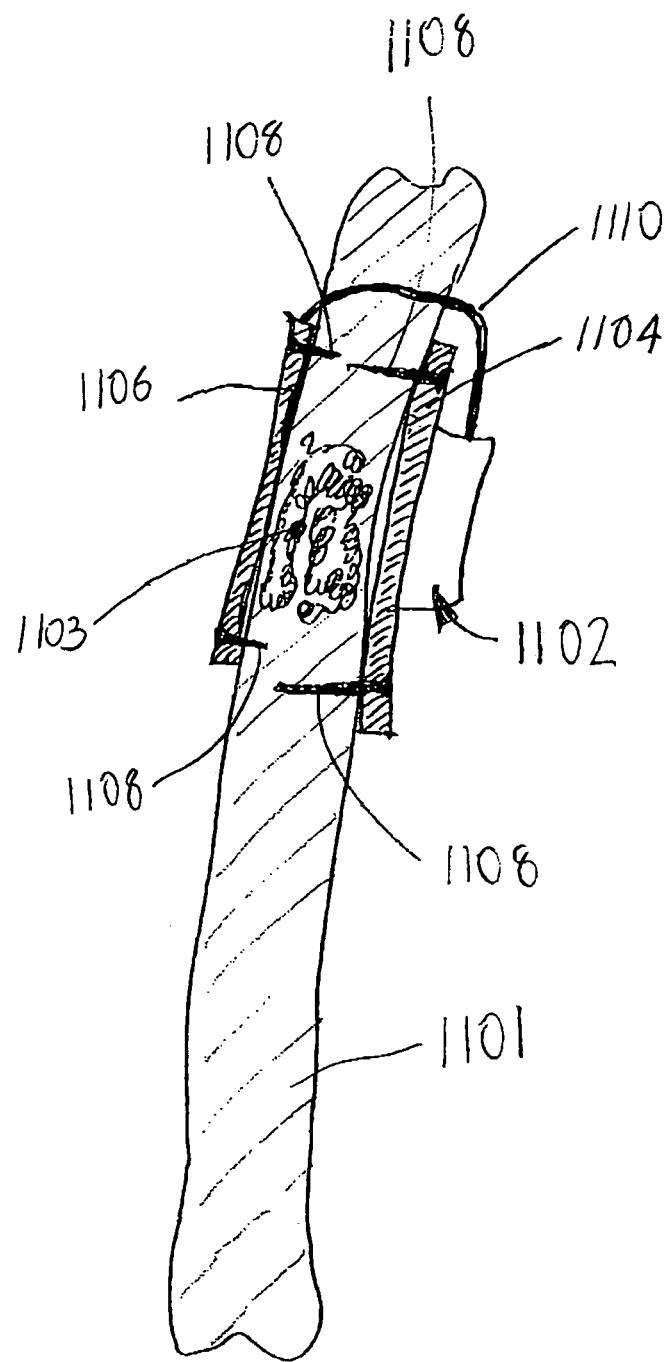
FIG. 11 is an exemplary application of electroporation cancer treatment in accordance with another embodiment of the present invention as it may be applied to treatment of osteosarcoma.

FIG. 11 illustrates yet another application of apparatus and methods of the present invention as they may be configured to treat osteosarcoma. A cross-sectional view of human or mammalian bone 1101 is shown in FIG. 11. After tumor tissue 1103 is surgically removed, osteosynthesis of the affected area may be carried out using steel plates 1104 and 1106 which secure to a healthy portion of bone 1101 with screws 1108 as is generally known in the art. IMD 1102, which may be similar in most respects both in construction and operation to IMD 600 illustrated in FIGS. 6-9, may be implanted proximate to or attach directly to plate 1104. Conductive lead 1110 may connect IMD 1102 to plate 1106. Plates 1104, 1106 are preferably conductive and operable to function in a manner similar to electrodes 605 and 614 of FIG. 6 described above. That is, a high strength electric field may be generated between plates 1104 and 1106, whereby electroporation therapy as described and illustrated herein may be delivered to the remaining bone tissue.

Other embodiments are also possible without departing from the scope of the invention. For example, other sensors, e.g., a pH sensor, may be incorporated to yield additional diagnostic information. A pH sensor would permit measuring of pH levels in and around the tumor tissue to monitor potential inflammatory edema. That is, downward trends in pH readings could indicate tissue inflammation or even infection. Incorporation of pH measurement into the algorithms for therapy control are certainly possible.

Another embodiment could include an X-ray sensor at a distal tip of a lead that is implanted within the tumor tissue (e.g., second lead 614 of FIG. 6). Radiotherapy of the tumor could be accomplished via X-ray irradiation from one or more angles with the implanted lead until the cumulative dose prescribed for the tumor volume is achieved.

Use of IMD apparatus described and illustrated herein may also permit detection of radiotherapy edema. Dosage and other therapy parameters could be stored in the IMD and retrieved by subsequent interrogation. As a result, more precise radiotherapy treatment may be achieved.

In still another embodiment, patient alert features may be incorporated into the apparatus and methods of the present invention. For example, detected edema brought on by electroporation therapy (or radiotherapy) may produce an alert, e.g., an audible sound. This sound would be a signal to the patient to contact his or her physician to investigate the edema before the condition worsens.

In still yet another embodiment, immune system sensors capable of measuring immune system response to cancer therapy may be included. For example, immunity trends could be determined and stored for subsequent interrogation. These trends could be used to manually reprogram the therapy profile or the trends could be used to dynamically alter the algorithm of the IMD during therapy, e.g., the immunity trends could provide a feedback to control cancer therapy delivery.

Thus, cancer treatment apparatus and methods of the present invention permit electroporation treatment of subcutaneous tumors utilizing implantable devices. Some embodiments may additionally include the ability to introduce chemotherapy drugs into the body at the prescribed therapy intervals. High frequency stimulation of tissue in or around the tumor may increase the temperature before electroporation therapy. Still further, edema detection may be incorporated into IMDs of the present invention. Edema detection may be used to suspend cancer therapy once a threshold edema value is detected.

Other advantages of IMDs and methods of the present invention include the ability to program most any therapy parameter. Programming offers medical personal the flexibility to dynamically alter treatment profiles, either manually or automatically (e.g., based on closed loop feedback signals), based on particular patient needs. Moreover, by implanting electroporation devices as described herein, continuous and periodic therapy may be delivered more precisely and with little or no external therapy apparatus required.

The complete disclosure of the patents, patent documents (including patent applications), and publications cited in the Background of the Invention, Detailed Description of the Preferred Embodiments, and elsewhere herein are incorporated by reference in their entirety as if each were individually incorporated.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the sensors described herein but may, as mentioned above, incorporate most any sensing device beneficial to the cancer therapy. The present invention further includes within its scope methods of making and using the devices described herein above.

What is claimed is:

1. A method for treating a cancerous tumor, comprising:
implanting a wholly-implantable electroporation device wholly within a body, wherein said wholly-implantable electroporation device includes a drug reservoir and operative control circuitry both disposed within a housing for said wholly-implantable electroporation device;
delivering a drug to the body and proximate the cancerous tumor via a fluid conduit coupled to the drug reservoir;
delivering from the wholly-implantable electroporation device, at least one electrical pulse across at least a portion of the cancerous tumor, wherein said at least one electrical pulse produces an electrical field strength of from about 700 V/cm to about 1500 V/cm and said at least one electrical pulse has a pulse width of from about 50 microseconds to about 200 microseconds; and
detecting a qRs complex from an electrocardiogram of the body and synchronizing the delivering of the at least one electrical pulse with the qRs complex.

2. The method of claim 1, further comprising:
sensing at least one biological parameter and providing a sense signal based on the biological parameter; and
conveying said parameter to said operative control circuitry disposed within the housing of the device.

3. The method of claim 2, further comprising controlling delivery of the at least one electrical pulse based on the sense signal.

4. The method of claim 1, further comprising measuring impedance across a portion of the cancerous tumor and comparing the impedance to a threshold impedance value.

5. The method of claim 4, further comprising suspending delivery of additional electrical pulses based on a result of comparing the impedance to the threshold impedance value.

6. The method of claim 1, wherein delivering the drug to the body comprises delivering the drug via an external drug delivery apparatus.

7. The method of claim 1, further comprising increasing a temperature of the body in the vicinity of the cancerous tumor prior to delivering the at least one electrical pulse.

8. The method of claim 7, wherein increasing the temperature of the body in the vicinity of the cancerous tumor comprises delivering a high frequency stimulus with the electroporation device.

9. The method of claim 1, further comprising programming the electroporation device to deliver a particular therapy profile.

10. The method of claim 9, wherein programming the electroporation device occurs after implantation.

11. A method for treating cancer, comprising:
implanting a wholly-implantable electroporation device in a body, the wholly-implantable electroporation device operable to selectively electroporate tissue within the body using at least one lead having at least one wholly implantable therapy electrode associated therewith; and
locating the at least one wholly implantable therapy electrode in or proximate a cancerous tumor;
applying a high frequency stimulus in the vicinity of the cancerous tumor with the at least one wholly-implantable first therapy electrode, thereby raising a temperature in the vicinity of the cancerous tumor;
delivering a drug to the body in the vicinity of the cancerous tumor; and delivering, with the wholly-implantable electroporation device, at least one electrical pulse in the vicinity of the cancerous tumor, wherein said at least one electrical pulse produces an electrical field strength of from about 700 V/cm to about 1500 V/cm and has a pulse width of from about 50 microseconds to about 200 microseconds; and
detecting a qRs complex from an electrocardiogram of the body and synchronizing the delivering of the at least one electrical pulse with the qRs complex.

12. The method of claim 11, further comprising sensing the temperature in the body and providing a sense signal based on the temperature.

13. The method of claim 11, further comprising measuring impedance across a portion of the cancerous tumor and comparing the impedance to a threshold impedance value.

14. The method of claim 13, comprising suspending delivery of additional electrical pulses based on a result of comparing the impedance to the threshold impedance value.

15. The method of claim 11, wherein delivering the drug to the body comprises delivering the drug through a drug catheter coupled to a housing of the electroporation device, the drug catheter in fluid communication with a drug reservoir located within the housing.

16. The method of claim 11, wherein delivering the drug to the body comprises delivering the drug via an external drug delivery apparatus.

17. The method of claim 11, wherein the cancerous tumor is a breast carcinoma.

18. The method of claim 11, wherein the cancerous tumor is a osteosarcoma.

19. The method of claim 11, wherein delivering the at least one electrical pulse comprises delivering about four to about eight electrical pulses.

* * * * *

UNITED STATES PATENT AND TRADEMARK OFFICE
CERTIFICATE OF CORRECTION

| | | |
|---|---|---|
| PATENT NO. | : 8,500,713 B2 | Page 1 of 1 |
| APPLICATION NO. | : 10/695848 | |
| DATED | : August 6, 2013 | |
| INVENTOR(S) | : Bozidar Ferek-Petric | |

It is certified that error appears in the above-identified patent and that said Letters Patent is hereby corrected as shown below:

In the Claims

Col. 18, line 23, delete "at least one wholly implantable therapy" and insert in place thereof -- at least one wholly-implantable therapy --.

Signed and Sealed this
Second Day of September, 2014

Michelle K. Lee
*Deputy Director of the United States Patent and Trademark Office*